United States Patent
Hakoshima

(10) Patent No.: US 11,023,039 B2
(45) Date of Patent: Jun. 1, 2021

(54) VISUAL LINE DETECTION APPARATUS AND VISUAL LINE DETECTION METHOD

(71) Applicant: JVC KENWOOD Corporation, Yokohama (JP)

(72) Inventor: Shuji Hakoshima, Yokohama (JP)

(73) Assignee: JVC KENWOOD Corporation, Yokohama (JP)

( * ) Notice: Subject to any disclaimer, the term of this patent is extended or adjusted under 35 U.S.C. 154(b) by 64 days.

(21) Appl. No.: 15/962,049

(22) Filed: Apr. 25, 2018

(65) Prior Publication Data

US 2018/0239427 A1 Aug. 23, 2018

Related U.S. Application Data

(63) Continuation of application No. PCT/JP2016/079358, filed on Oct. 3, 2016.

(30) Foreign Application Priority Data

Dec. 1, 2015 (JP) .............................. JP2015-235181

(51) Int. Cl.
*G06F 3/01* (2006.01)
*A61B 3/113* (2006.01)
(Continued)

(52) U.S. Cl.
CPC .............. *G06F 3/013* (2013.01); *A61B 3/113* (2013.01); *G06K 9/0061* (2013.01); *G06T 7/73* (2017.01);
(Continued)

(58) Field of Classification Search
CPC . G06F 3/013; G06T 7/73; G06T 2207/30201; G06K 9/0061; A61B 3/113; A61B 3/107; A61B 3/111; A61B 3/112
See application file for complete search history.

(56) References Cited

U.S. PATENT DOCUMENTS

| 2005/0175218 A1* | 8/2005 | Vertegaal | A61B 3/113 382/103 |
| 2010/0328444 A1* | 12/2010 | Blixt | A61B 3/113 348/78 |

(Continued)

FOREIGN PATENT DOCUMENTS

JP 2739331 1/1998

OTHER PUBLICATIONS

International Search Report and Written Opinion for International Patent Application No. PCT/JP2016/079358 dated Dec. 20, 2016, 7 pages.

*Primary Examiner* — Sahlu Okebato
(74) *Attorney, Agent, or Firm* — Amin, Turocy & Watson, LLP

(57) ABSTRACT

A visual line detection apparatus includes a light source, a position detection unit configured to detect positions of pupil centers and positions of corneal reflection centers, a curvature radius calculation unit configured to calculate corneal curvature radii from a position of the light source and the positions of the corneal reflection centers, a viewpoint detection unit configured to detect viewpoints from the positions of the pupil centers and the corneal curvature radii, an extraction unit configured to extract pupil parameters indicating sizes of the pupils of the right and left respective eyeballs from the image of the eyeballs, and a correction unit configured to correct the viewpoint of the left eyeball and the viewpoint of the right eyeball on the basis of the pupil parameters and calculate a synthesized viewpoint.

6 Claims, 15 Drawing Sheets

(51) Int. Cl.
*G06K 9/00* (2006.01)
*G06T 7/73* (2017.01)
*A61B 3/11* (2006.01)
*A61B 3/107* (2006.01)

(52) U.S. Cl.
CPC ............... *A61B 3/107* (2013.01); *A61B 3/111* (2013.01); *A61B 3/112* (2013.01); *G06T 2207/30201* (2013.01)

(56) References Cited

U.S. PATENT DOCUMENTS

| | | | |
|---|---|---|---|
| 2011/0205491 A1* | 8/2011 | Koiwa | A61B 3/18 351/206 |
| 2013/0188834 A1* | 7/2013 | Ebisawa | A61B 3/113 382/103 |
| 2015/0009313 A1* | 1/2015 | Noda | H04N 5/23293 348/78 |
| 2016/0150956 A1 | 6/2016 | Hakoshima et al. | |
| 2020/0094818 A1* | 3/2020 | Li | A61B 5/0476 |

* cited by examiner

VISUAL LINE DETECTION APPARATUS AND VISUAL LINE DETECTION METHOD

CROSS-REFERENCE TO RELATED APPLICATION(S)

This application is a continuation of International Application No. PCT/JP2016/079358, filed on Oct. 3, 2016, which claims the benefit of priority of the prior Japanese Patent Application No. 2015-235181, filed on Dec. 1, 2015, the entire contents of which are incorporated herein by reference.

FIELD

The present invention relates to a visual line detection apparatus and a visual line detection method.

BACKGROUND

Visual line detection apparatuses that detect a position that an operator or a subject gazes at, on an observation surface such as a monitor screen, have been proposed. As a method for detecting a visual line direction of a subject in a non-contact manner without attaching a device to the face, there is a method for irradiating an eyeball of the subject with detection light, calculating a pupil center and a corneal curvature center from an image of the eyeball irradiated with the detection light, and detecting a vector from the corneal curvature center toward the pupil center as the visual line direction of the subject.

CITATION LIST

Patent Literature

Patent Literature 1: Japanese Patent No. 2739331

SUMMARY

Technical Problem

The pupil center is calculated from the image of the eyeball. If the pupil center is not accurately calculated, accurate detection of a viewpoint of the subject becomes difficult.

Solution to Problem

Present disclosure comprises: a light source configured to irradiate an eyeball of a subject with detection light; a position detection unit configured to detect positions of pupil centers indicating centers of pupils of right and left respective eyeballs and positions of corneal reflection centers indicating centers of corneal reflexes from an image of the eyeballs irradiated with the detection light; a curvature radius calculation unit configured to calculate corneal curvature radii of the right and left respective eyeballs from a position of the light source and the positions of the corneal reflection centers; a viewpoint detection unit configured to detect viewpoints of the right and left respective eyeballs from the positions of the pupil centers and the corneal curvature radii; an extraction unit configured to extract pupil parameters indicating sizes of the pupils of the right and left respective eyeballs from the image of the eyeballs; and a correction unit configured to correct the viewpoint of the left eyeball and the viewpoint of the right eyeball on the basis of the pupil parameters so as to calculate a synthesized viewpoint.

DESCRIPTION OF EMBODIMENTS

Figure 1:
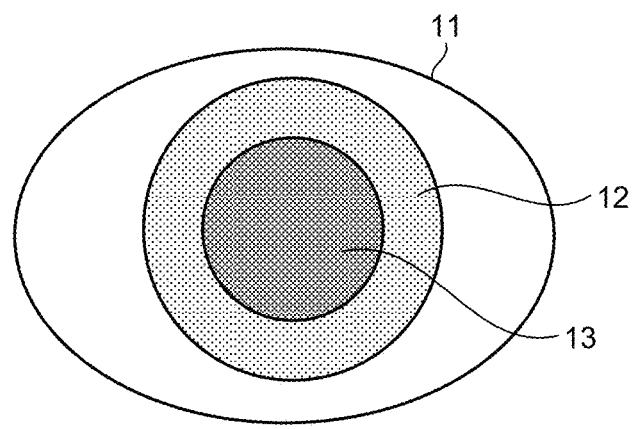
FIG. 1 is a diagram illustrating a state of an eye of a subject in a case of using one light source.

Hereinafter, an embodiment of a visual line detection apparatus and a visual line detection method according to the present invention will be described in detail with reference to the drawings. Note that the present invention is not limited by this embodiment. Hereinafter, an example of using a visual line detection apparatus for a diagnosis support apparatus that supports diagnosis of a subject, using a visual line detection result, will be described. Applicable apparatuses are not limited to diagnosis support apparatuses.

The visual line detection apparatus of the present embodiment detects visual line using illumination units installed at two places. Further, the visual line detection apparatus of the present embodiment calculates a position of a corneal curvature center and a corneal curvature radius with high precision using a result measured by causing the subject to gaze at one point before detecting the visual line.

Note that the illumination unit is an element including a light source and capable of irradiating the eyeball of the subject with light. The light source is an element that generates light, such as a light emitting diode (LED), for example. The light source may be constituted by one LED, or may be constituted by a combination of a plurality of LEDs arranged in one place. Hereinafter, the "light source" may be used as a term expressing the illumination unit.

To detect the viewpoint with high precision, it is important to properly detect a position of a pupil. It is known that, in the case of turning on a near-infrared light source and performing a capture with a camera, the pupil becomes darker than other portions when the camera and the light source are separated by a certain distance or more. The pupil position is detected using this characteristic.

In the present embodiment, with respect to two cameras, light sources are arranged at two positions outside the respective cameras. Then, the two light sources are turned on at different timings from each other, and the camera at a longer distance (more distant) from the light source turned on performs a capture. Accordingly, the pupil can be more darkly captured so that the pupil can be distinguished from other portions with high precision.

In this case, the light source to be turned on is different, and thus three-dimensional measurement by an ordinary stereo method cannot be simply applied. That is, a straight line connecting the light source and corneal reflex in obtaining the viewpoint cannot be calculated by world coordinates. Therefore, in the present embodiment, the mutual positional relationship between the cameras used for capture and the mutual positional relationship between the light sources to be turned on at the two timings are made symmetrical with respect to a virtual light source position representing a position of a virtual light source. Then, two coordinate values obtained at turning on the two respective light sources are converted into the world coordinates as a coordinate value by a left camera and a coordinate value by a right camera. Accordingly, it is possible to calculate the straight line connecting the virtual light source and the corneal reflex by the world coordinates using the positions of the corneal reflexes obtained at turning on the two respective light sources, and to calculate the viewpoint based on the straight line.

Figure 2:
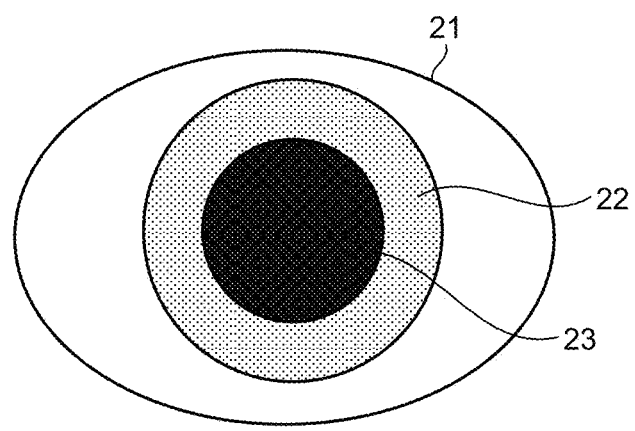
FIG. 2 is a diagram illustrating a state of an eye of a subject in a case of using two light sources.

FIG. 1 is a diagram illustrating a state of an eye 11 of a subject in a case of using one light source. As illustrated in FIG. 1, a difference in darkness between an iris 12 and a pupil 13 is not sufficient, and it is difficult to distinguish the iris 12 and the pupil 13. FIG. 2 is a diagram illustrating a state of an eye 21 of a subject in a case of using two light sources. As illustrated in FIG. 2, a difference in darkness between an iris 22 and a pupil 23 is larger than that in FIG. 1.

Figure 3:
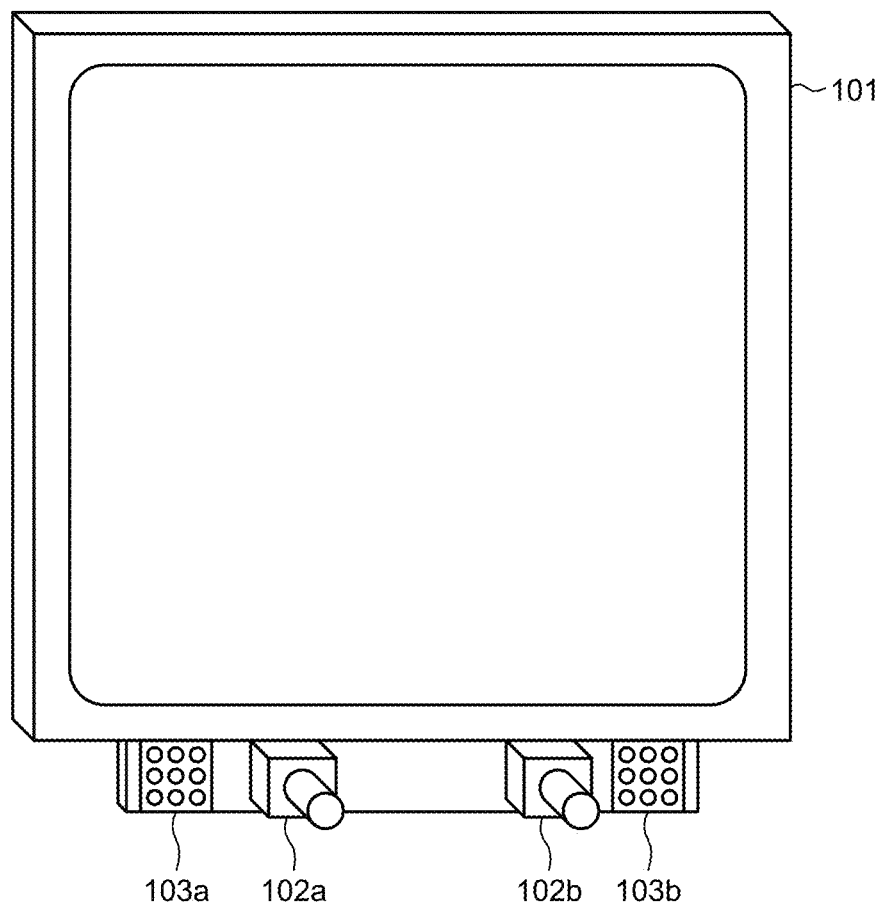
FIG. 3 is a diagram illustrating an example of arrangement of a display unit, a stereo camera, an infrared light source, and a subject of the present embodiment.
Figure 4:
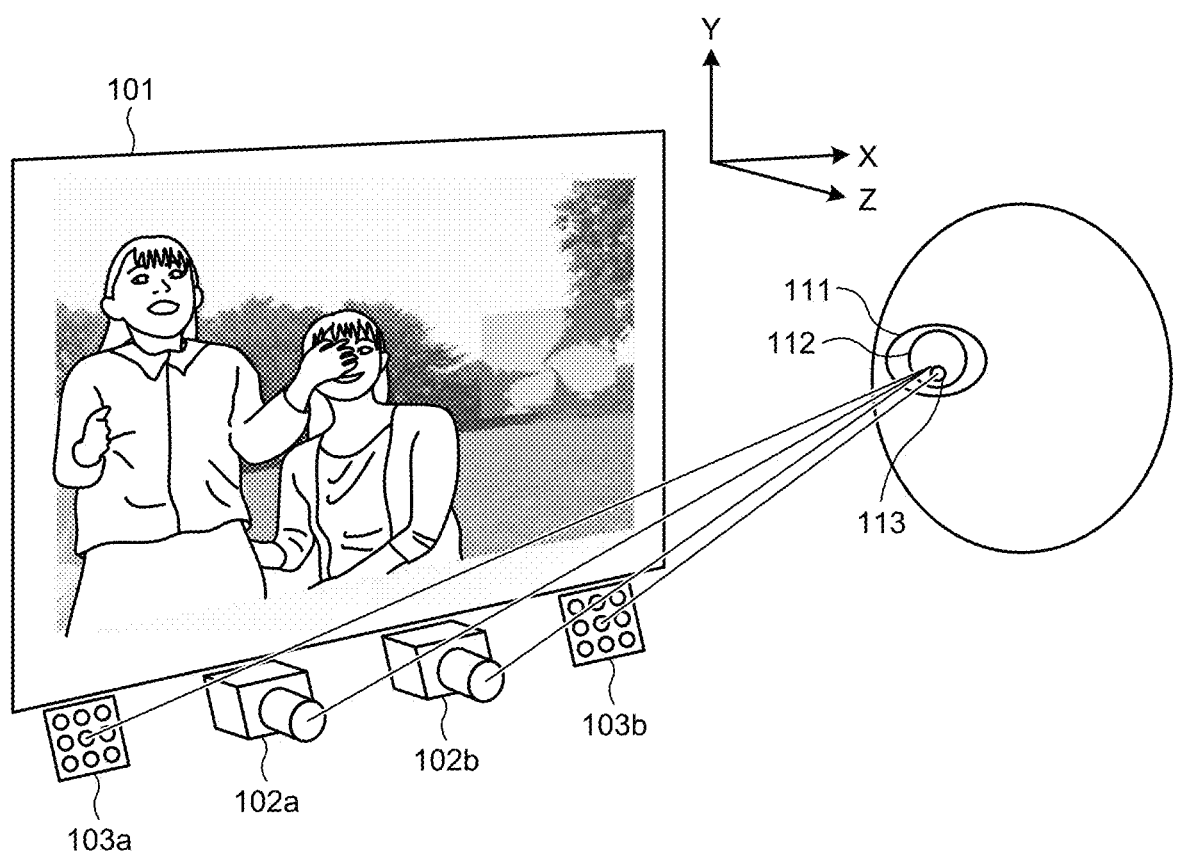
FIG. 4 is a diagram illustrating an example of arrangement of a display unit, a stereo camera, an infrared light source, and a subject of the present embodiment.

FIGS. 3 and 4 are diagrams illustrating examples of arrangement of a display unit, a stereo camera, an infrared light source, and a subject of the present embodiment.

As illustrated in FIG. 3, the diagnosis support apparatus of the present embodiment includes a display unit 101, a right camera 102a and a left camera 102b comprising a stereo camera, and LED light sources 103a and 103b. The right camera 102a and the left camera 102b are arranged below the display unit 101. The LED light sources 103a and 103b are arranged outside the right camera 102a and the left camera 102b, respectively. The LED light sources 103a and 103b are light sources that radiate near-infrared rays having a wavelength of 850 [nm], for example. FIG. 3 illustrates an example in which nine LEDs comprise each of the LED light sources 103a and 103b. The right camera 102a and the left camera 102b can be used with a lens capable of transmitting the near-infrared light having a wavelength of 850 [nm].

Note that the positions of the LED light sources 103a and 103b and the positions of the right camera 102a and the left camera 102b may be switched, and the LED light sources 103a and 103b may be arranged at inner positions of the right camera 102a and the left camera 102b, respectively.

As illustrated in FIG. 4, the LED light sources 103a and 103b irradiate an eyeball 111 of the subject with the near-infrared light as detection light. The left camera 102b performs a capture when the LED light source 103a is radiated, and the right camera 102a performs a capture when the LED light source 103b is radiated. By appropriately setting the positional relationship between the right camera 102a and the left camera 102b and the LED light sources 103a and 103b, a pupil 112 is reflected with low luminance and becomes dark, and corneal reflex 113, which is caused as a virtual image in the eyeball 111, is reflected with high luminance and becomes bright, in a captured image. Therefore, the positions on the image of the pupil 112 and corneal reflex 113 can be acquired by the two cameras (the right camera 102a and the left camera 102b).

Further, three-dimensional world coordinate values of the positions of the pupil 112 and the corneal reflex 113 are calculated from the positions of the pupil 112 and the corneal reflex 113 obtained by the two cameras. In the present embodiment, as the three-dimensional world coordinates, a center position of a screen of the display unit 101 is set to an origin, an up and down direction represents a Y coordinate (the up direction is +), a cross direction represents an X coordinate (the observers' right is +), and a depth direction represents a Z coordinate (the front side is +).

Figure 5:
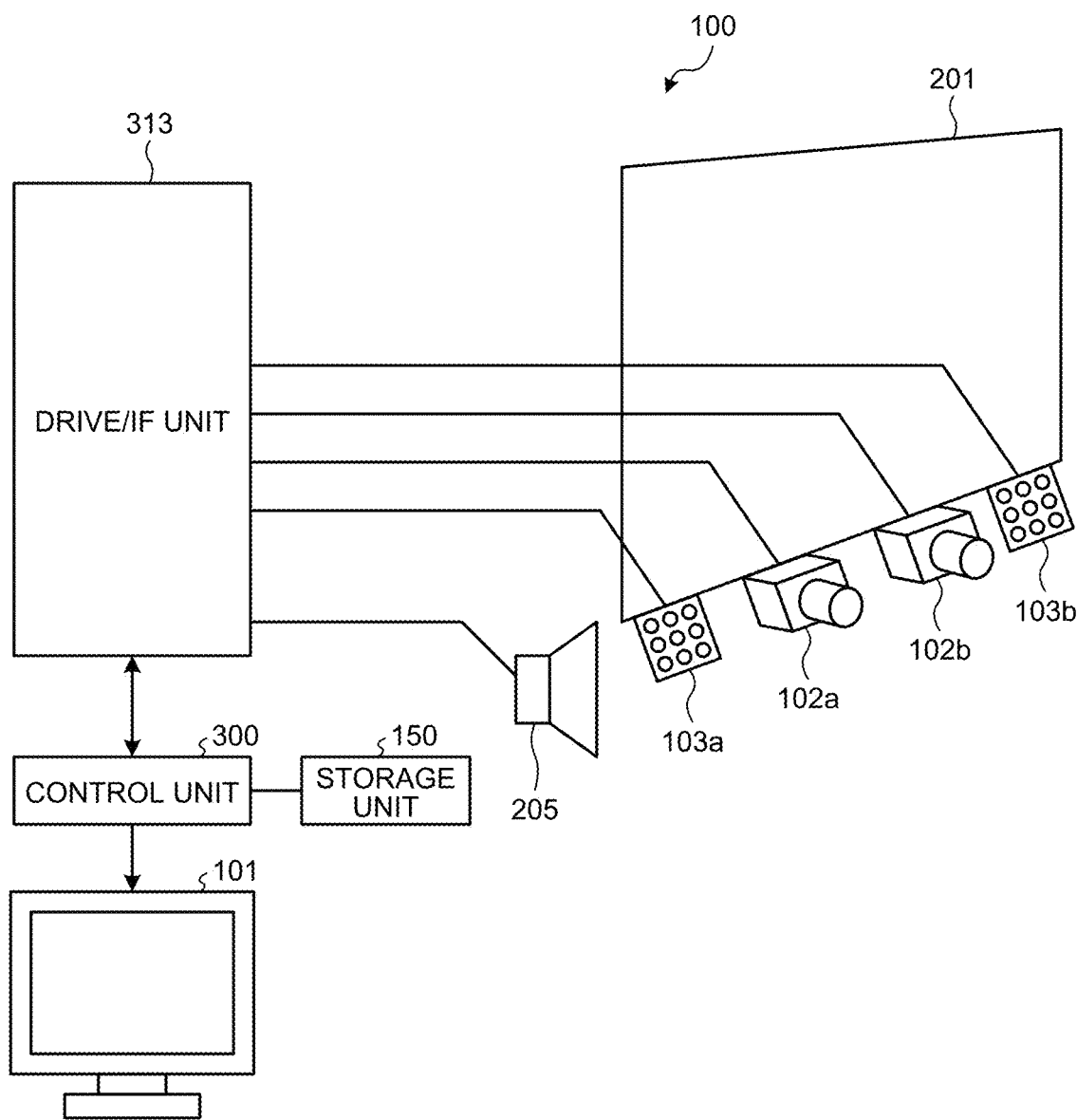
FIG. 5 is a diagram illustrating an outline of functions of a diagnosis support apparatus.

FIG. 5 is a diagram illustrating an outline of functions of a diagnosis support apparatus 100. FIG. 5 illustrates part of the configurations illustrated in FIGS. 3 and 4 and configurations used to drive the configurations. As illustrated in FIG. 5, the diagnosis support apparatus 100 includes the right camera 102a, the left camera 102b, the LED light source 103a for the left camera 102b, the LED light source 103b for the right camera 102a, a speaker 205, a drive/interface (IF) unit 313, a control unit 300, a storage unit 150, and the display unit 101. In FIG. 5, a display screen 201 is illustrated easy to understand the positional relationship between the right camera 102a and the left camera 102b, but the display screen 201 is a screen displayed on the display unit 101. Note that the drive unit and the IF unit may be an integrated unit or may be separate units.

The speaker 205 functions as a sound output unit that outputs a sound or the like for calling attention to the subject at the time of calibration or the like.

The drive/IF unit 313 drives the units included in the stereo camera. Further, the drive/IF unit 313 is an interface between the units included in the stereo camera and the control unit 300.

The control unit 300 can be realized by a computer including a control device such as a central processing unit (CPU), a storage device such as a read only memory (ROM) and a random access memory (RAM), a communication IF connected to a network and performing communication, and a bus connecting the units.

The storage unit 150 stores various types of information such as a control program, a measurement result, and a diagnosis support result. The storage unit 150 stores an image to be displayed on the display unit 101, and the like, for example. The display unit 101 displays various types of information such as a target image for diagnosis.

Figure 6:
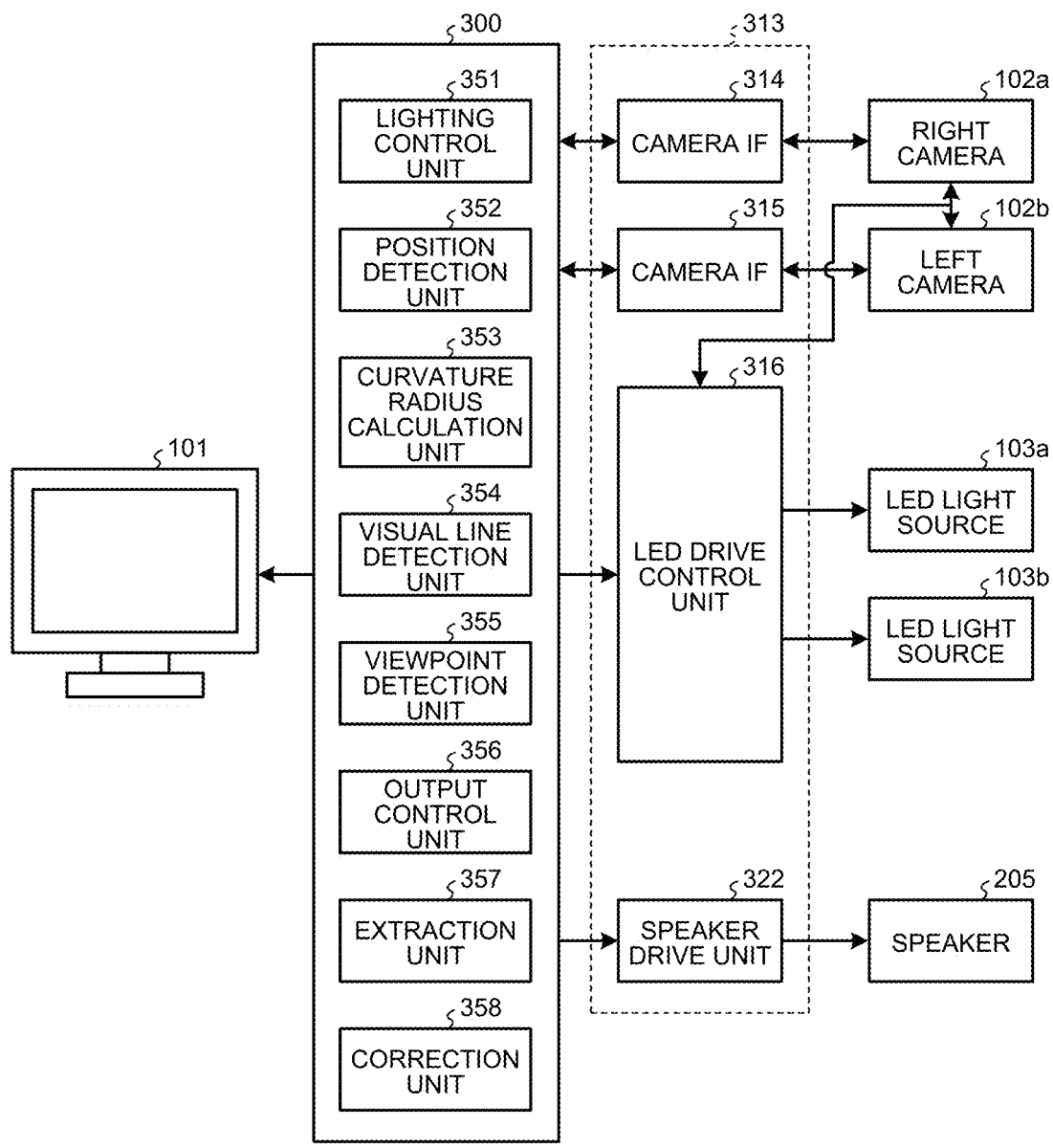
FIG. 6 is a block diagram illustrating an example of detailed functions of units illustrated in FIG. 5.

FIG. 6 is a block diagram illustrating an example of detailed functions of the units illustrated in FIG. 5. As illustrated in FIG. 6, the display unit 101 and the drive/IF unit 313 are connected to the control unit 300. The drive/IF unit 313 includes camera IFs 314 and 315, an LED drive control unit 316, and a speaker drive unit 322.

The right camera 102a and the left camera 102b are connected to the drive/IF unit 313 via the camera IFs 314 and 315, respectively. The drive/IF unit 313 drives these cameras to image the subject. A frame synchronization signal is output from the right camera 102a. The frame synchronization signal is input to the left camera 102b and the LED drive control unit 316. As a result, the LED light sources 103a and 103b are emitted, and images by the right and left cameras are taken in corresponding to that.

The speaker drive unit 322 drives the speaker 205. Note that the diagnosis support apparatus 100 may include an interface (printer IF) for being connected with a printer as a printing unit. Further, a printer may be provided in the diagnosis support apparatus 100.

The control unit 300 controls the entire diagnosis support apparatus 100. The control unit 300 includes a lighting control unit 351, a position detection unit 352, a curvature radius calculation unit 353, a visual line detection unit 354, a viewpoint detection unit 355, an output control unit 356, an extraction unit 357, and a correction unit 358.

The elements (the lighting control unit 351, the position detection unit 352, the curvature radius calculation unit 353, the visual line detection unit 354, the viewpoint detection unit 355, the output control unit 356, the extraction unit 357, and the correction unit 358) included in the control unit 300 may be realized by software (a program), by a hardware circuit, or by use of software and a hardware circuit in combination.

In the case of realizing the elements by a program, the program is recorded in an installable format file or an executable format file in a recording medium capable of read by a computer such as a compact disk read only memory (CD-ROM), a flexible disk (FD), a compact disk recordable (CD-R), or a digital versatile disk (DVD), and is provided as a computer program product. The program may be stored on a computer connected to a network such as the Internet and provided by being downloaded via the network. Alternatively, the program may be provided or distributed via a network such as the Internet. Alternatively, the program may be provided by being incorporated in a ROM or the like in advance.

The lighting control unit 351 controls lighting of the LED light sources 103a and 103b, using the LED drive control unit 316. For example, the lighting control unit 351 controls the LED light sources 103a and 103b to be turned on at different timings from each other. The timing difference (period of time) may be a time determined in advance as a time during which an influence is not caused on a visual line detection result due to movement of the visual line of the subject or the like.

The position detection unit 352 detects pupil areas indicating pupils of right and left respective eyeballs, and corneal reflex areas indicating corneal reflexes of the right and left respective eyeballs, from images of the right and left eyeballs of the subject imaged by the stereo camera being irradiated with near-infrared light. Further, the position detection unit 352 detects positions of pupil centers indicating centers of the pupils of the right and left respective eyeballs on the basis of the pupil areas. For example, the position detection unit 352 selects a plurality of points on a contour of the pupil area, and calculates a center of a circle passing through the plurality of selected points as the position of the pupil center. Similarly, the position detection unit 352 detects positions of corneal reflection centers indicating centers of the corneal reflexes of the right and left respective eyeballs on the basis of the corneal reflex areas.

The curvature radius calculation unit 353 calculates a position of a corneal curvature center from a first straight line connecting a virtual light source position and the corneal reflection center. Further, the curvature radius calculation unit 353 calculates corneal curvature radii from the virtual light source position and the positions of the corneal reflection centers, the corneal curvature radii are distances between corneal surfaces and the corneal curvature centers of the right and left respective eyeballs of the subject.

The curvature radius calculation unit 353 calculates an intersection point of a second straight line and the first straight line using the pupil center and the corneal reflection center calculated when the subject is caused to gaze at the target position. The second straight line is connecting the pupil center and the target position, and the first straight line is connecting the corneal reflection center and the virtual light source position. The intersection point calculated is the corneal curvature center. The curvature radius calculation unit 353 calculates a distance between the pupil center and the corneal curvature center, and stores the distance in the storage unit 150. Further, the curvature radius calculation unit 353 calculates the corneal curvature radius that is the distance between the corneal surface and the corneal curvature center, and stores the corneal curvature radius in the storage unit 150.

The target position may be determined in advance, and any position may be employed as long as the three-dimensional world coordinate values can be calculated. For example, a center position of the display screen 201 (the origin of three-dimensional world coordinates) can be set as the target position. In this case, for example, the output control unit 356 displays a target image or the like for causing the subject to gaze at, at the target position (center position) on the display screen 201. Accordingly, it is possible to cause the subject to gaze at the target position.

The target image may be any image as long as the image can attract the subject's attention. For example, an image with a display mode such as luminance and color that changes, or an image with a display mode that is different from other areas can be used as the target image.

Note that the target position is not limited to the center position of the display screen 201 and may be any position. In a case the center position of the display screen 201 is set as the target position, the distance to an arbitrary end portion of the display screen 201 becomes minimum. Therefore, a measurement error at the time of detecting the visual line can be further reduced, for example.

The processing up to the calculation of the distance between the pupil center and the corneal curvature center and the calculation of the corneal curvature radius is executed in advance by the time of the start of actual visual line detection, for example. When detecting the visual line, the curvature radius calculation unit 353 can calculate a position, as the corneal curvature center, where the distance from the pupil center becomes the distance calculated in advance, on the first straight line connecting the virtual light source position and the corneal reflection center. The curvature radius calculation unit 353 calculates the position of the corneal curvature center from the virtual light source position, a predetermined position indicating the target image on the display unit, the position of the pupil center, and the position of the corneal reflection center, and calculates the corneal curvature radius.

The visual line detection unit 354 detects visual line directions of the right and left respective eyeballs of the subject from the positions of the pupil centers, and the positions of the corneal curvature radii or of the corneal curvature centers. For example, the visual line detection unit 354 detects a direction from the corneal curvature center to the pupil center as the visual line direction of the subject.

The viewpoint detection unit 355 detects viewpoints of the right and left respective eyeballs of the subject from the visual line directions detected from the positions of the pupil centers, and the corneal curvature radii or the positions of the corneal curvature centers in the visual line detection unit 354. The viewpoint detection unit 355 detects, for example, a viewpoint (gaze point) that the subject gazes on the display screen 201. The viewpoint detection unit 355 detects an intersection point between a visual line vector and an XY plane expressed by a three-dimensional world coordinate system as illustrated in FIG. 4, as the viewpoint of the subject.

The extraction unit 357 extracts pupil parameters indicating sizes of the pupils of the right and left respective eyeballs from the images of the right and left eyeballs of the subject captured by the right and left cameras. In the present embodiment, the pupil parameters are areas of the pupils of the right and left respective eyeballs acquired in the images captured by the right and left cameras. The extraction unit 357 extracts the area of the pupil of the left eyeball and the area of the pupil of the right eyeball from the images of the right and left eyeballs of the subject.

The correction unit 358 corrects, on the basis of the pupil parameters, the viewpoint of the right eyeball and the viewpoint of the left eyeball detected by the viewpoint detection unit 355 so as to calculate a synthesized viewpoint.

The output control unit 356 controls outputs of various types of information to the display unit 101, the speaker 205, and the like. In the present embodiment, the output control unit 356 displays, on the display unit 101, the synthesized viewpoint of the subject calculated in the correction unit 358. Further, the output control unit 356 displays the target image at the target position on the display unit 101. Further, the output control unit 356 controls outputs of a diagnostic image, an evaluation result by an evaluation unit, and the like to the display unit 101.

Figure 7:
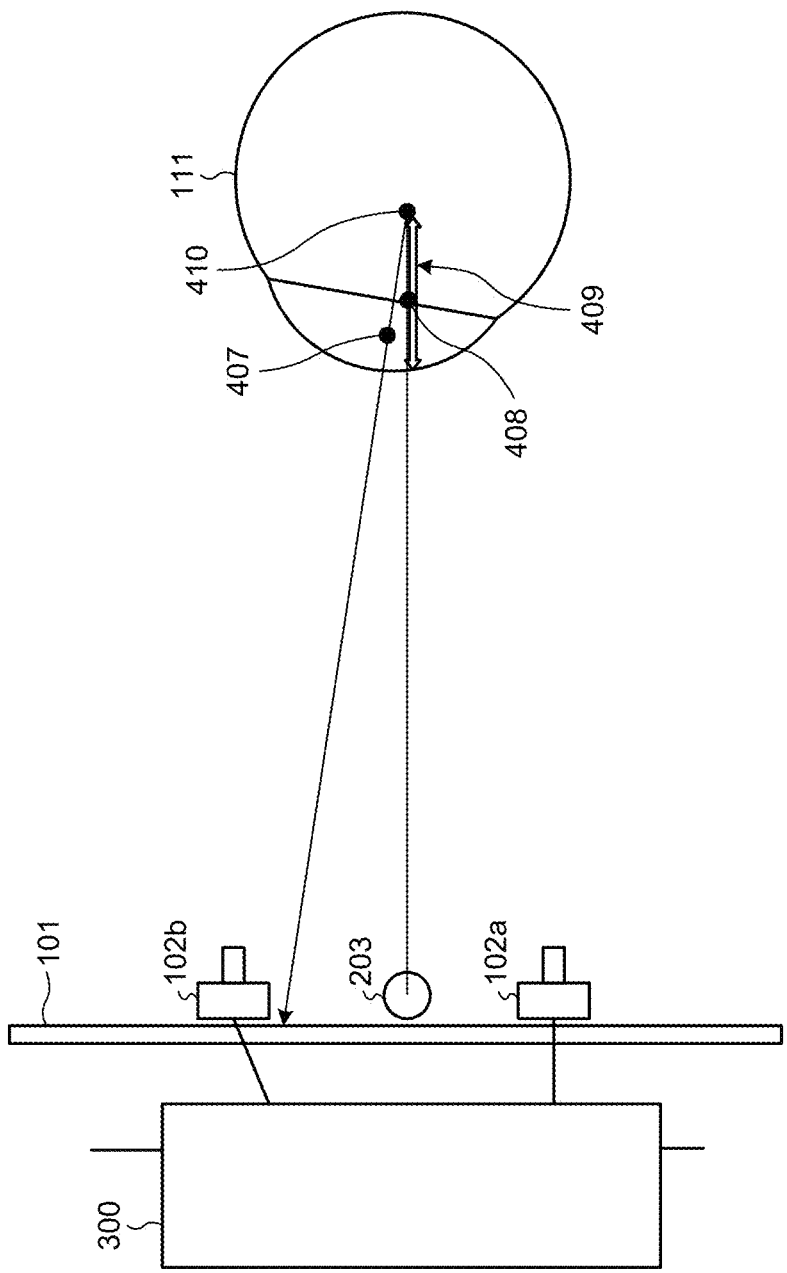
FIG. 7 is a diagram for describing an outline of processing in a case of assuming that one light source is used.

FIG. 7 is a diagram for describing an outline of processing in a case of assuming that one light source is used. The same reference numerals are given to elements that have been described in FIGS. 3 to 6, and description of the elements is omitted. In the example of FIG. 7, one LED light source 203 is used in place of the two LED light sources 103a and 103b.

A pupil center 407 and a corneal reflection center 408 respectively represent the pupil center and the corneal reflection center detected when the one LED light source 203 is turned on. The corneal reflection center 408 exists on a straight line connecting the LED light source 203 and a corneal curvature center 410, and the position of the corneal reflection center 408 appears at a midpoint between the corneal curvature center 410 and the corneal surface. A corneal curvature radius 409 represents the distance from the corneal surface to the corneal curvature center 410. Although the LED light source 203 is one LED here, a combination of several small LEDs may be arranged at one place.

Figure 8:
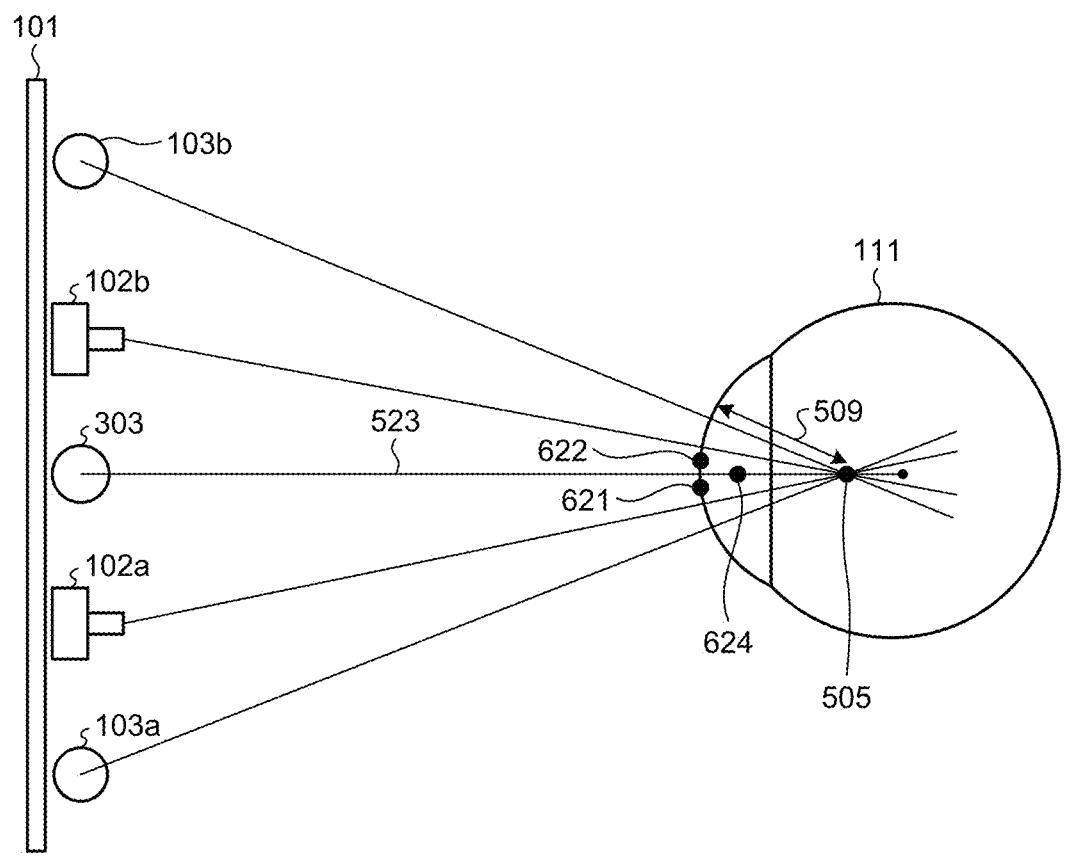
FIG. 8 is a diagram for describing an outline of processing executed by the diagnosis support apparatus of the present embodiment.

FIG. 8 is a diagram for describing an outline of processing executed by the diagnosis support apparatus 100 of the present embodiment. The same reference numerals are given to elements that have been described in FIGS. 3 to 6, and description of the elements is omitted.

A corneal reflection point 621 represents a corneal reflection point on an image when the left camera 102b captures the image. A corneal reflection point 622 represents a corneal reflection point on an image when the right camera 102a captures the image. In the present embodiment, the right camera 102a and the LED light source 103b for the right camera, and the left camera 102b and the LED light source 103a for the left camera are in a right and left symmetrical positional relationship with respect to a straight line passing through an intermediate position between the right camera 102a and the left camera 102b. Therefore, a virtual light source 303 can be regarded to be at the intermediate position (virtual light source position) between the right camera 102a and the left camera 102b. A corneal reflection point 624 represents a corneal reflection point corresponding to the virtual light source 303. World coordinate values of the corneal reflection point 624 is calculated by converting a coordinate value of the corneal reflection point 621 and a coordinate value of the corneal reflection point 622, using conversion parameters for converting coordinate values of the right and left cameras into three-dimensional world coordinates. A corneal curvature center 505 exists on a straight line 523 connecting the virtual light source 303 and the corneal reflection point 624. When the position of the corneal curvature center 505 and the position of the corneal surface are calculated, a corneal curvature radius 509 is calculated. In this manner, viewpoint detection can be performed by an equivalent method to the visual line detection method using the light source at one place illustrated in FIG. 7.

Note that the positional relationship between the right camera 102a and the left camera 102b, and the positional relationship between the LED light source 103a and the LED light source 103b are not limited to the above-described positional relationships. For example, the positional relationships may be right and left symmetrical with respect to the same straight line, or the right camera 102a and the left camera 102b, and the LED light source 103a and the LED light source 103b may not be arranged on the same straight line.

Figure 9:
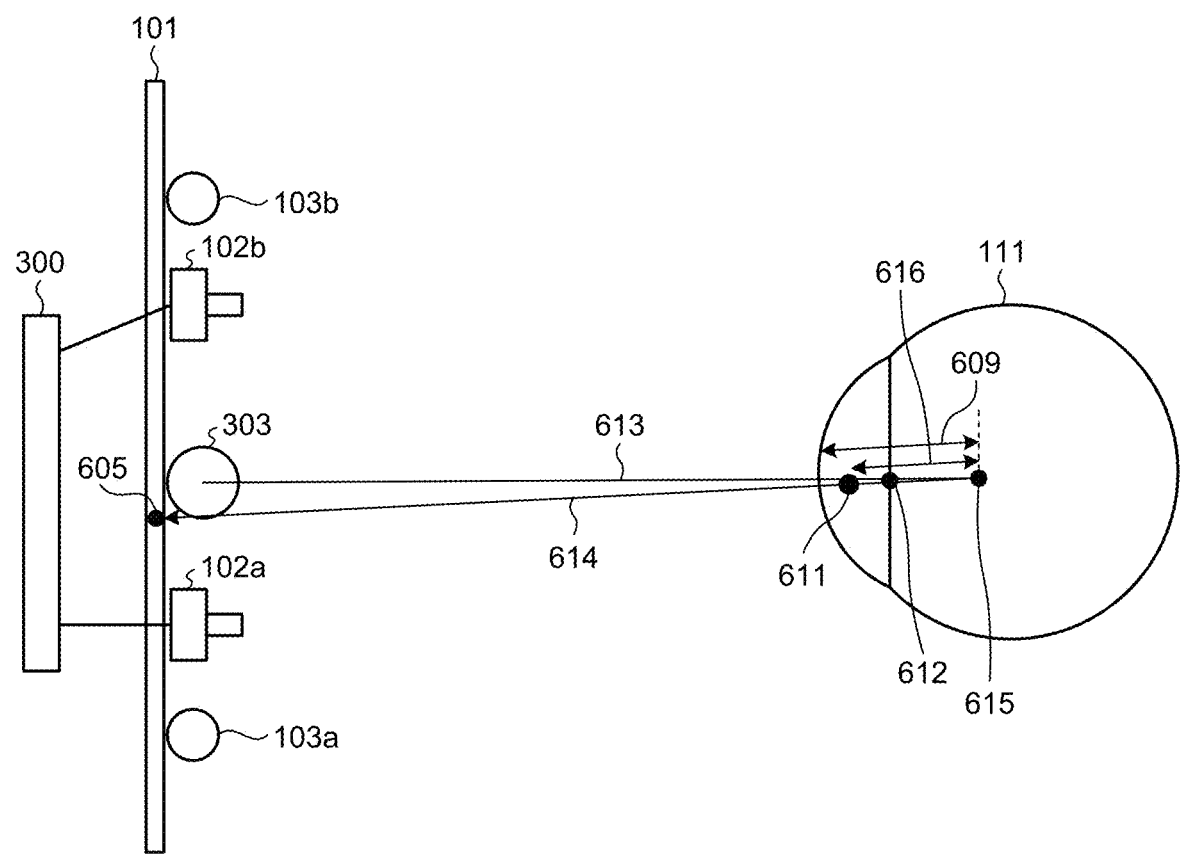
FIG. 9 is a diagram for describing calibration processing for calculating a distance between a pupil center position and a corneal curvature center position.

FIG. 9 is a diagram for describing calibration processing for calculating a position of a corneal curvature center 615, and a distance 616 between a position of a pupil center 611 and the position of the corneal curvature center 615, before detecting visual line or viewpoint. The same reference numerals are given to elements that have been described in FIGS. 3 to 6, and description of the elements is omitted.

A target position 605 is a position that is one point on the display unit 101, where the target image or the like is output and causing the subject to gaze at. In the present embodiment, the target position 605 is a center position on a screen of the display unit 101. A straight line 613 is a straight line connecting the virtual light source 303 and a corneal reflection center 612. A straight line 614 is a straight line connecting the target position 605, which is a gaze point that the subject gazes at, and the pupil center 611. The corneal curvature center 615 is an intersection point of the straight line 613 and the straight line 614. A corneal curvature radius 609 is a distance between the corneal surface and the corneal curvature center 615. The curvature radius calculation unit 353 calculates the distance 616 between the pupil center 611 and the corneal curvature center 615, and the corneal curvature radius 609, and stores them in the storage unit 150.

Figure 10:
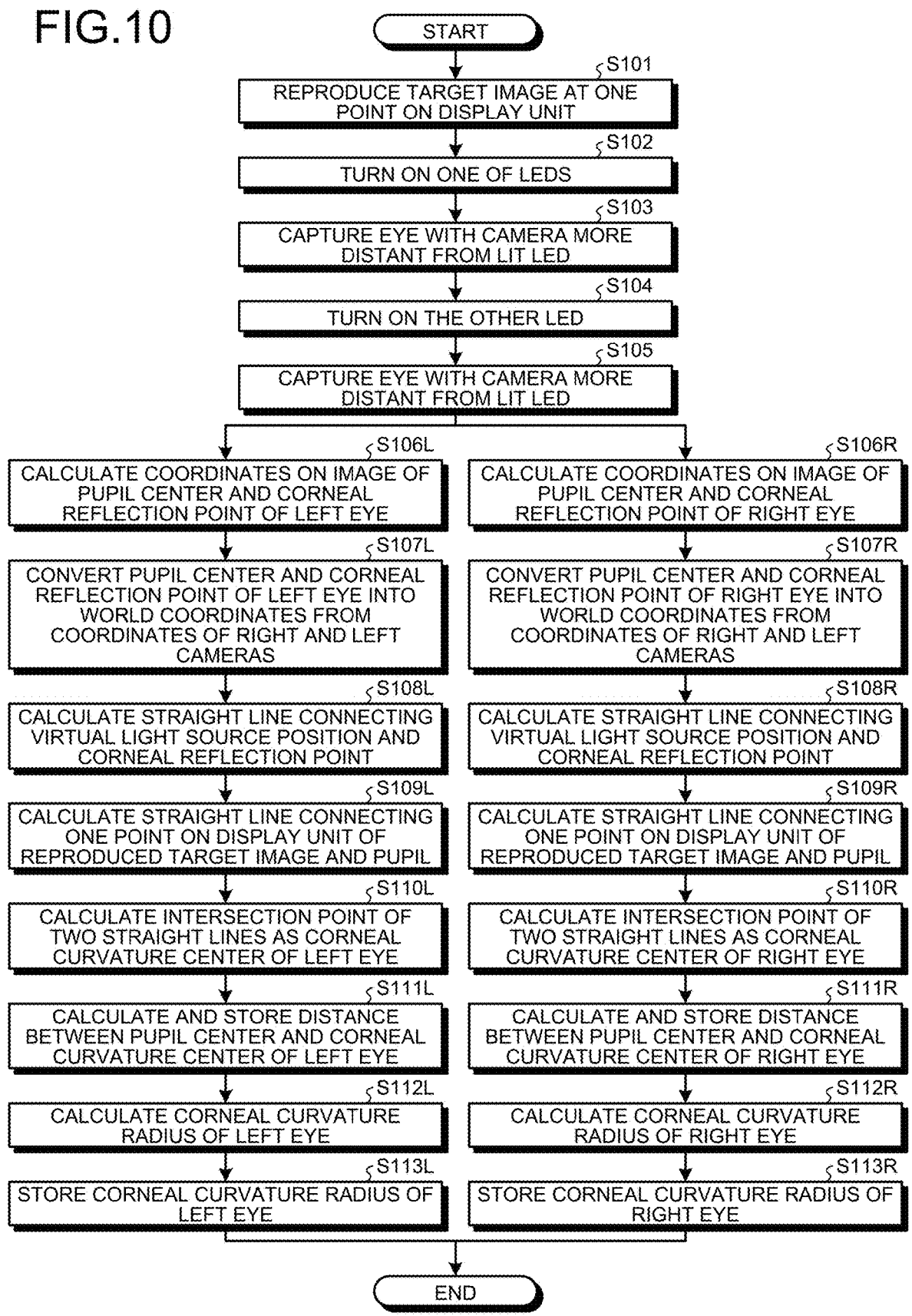
FIG. 10 is a flowchart illustrating an example of the calibration processing of the present embodiment.

FIG. 10 is a flowchart illustrating an example of the calibration processing of the present embodiment. The output control unit 356 reproduces the target image at one point on the screen of the display unit 101 (Step S101), and causes the subject to gaze at the one point. Next, the lighting control unit 351 turns on one of the LED light sources 103a and 103*b* toward the eye of the subject, using the LED drive control unit 316 (Step S102). The control unit 300 captures an image of the subject's eye with a camera having a longer distance from the lit LED light source between the right and left cameras (the right camera 102*a* and the left camera 102*b*) (Step S103). Next, the lighting control unit 351 turns on the other of the LED light sources 103*a* and 103*b* toward the eye of the subject (Step S104). The control unit 300 captures an image of the subject's eye with a camera having a longer distance from the lit LED light source between the right and left cameras (Step S105).

Note that it is not necessary to stop imaging by a camera other than the camera having a longer distance from the lit LED light source. That is, it is sufficient if the subject's eye is imaged with at least the camera having a longer distance from the lit LED light source, and the captured image can be used for coordinate calculation or the like.

After Step S105, processing for the left eye that is the left eyeball and processing for the right eye that is the right eyeball are separately performed. First, the calibration processing for the left eye will be described.

The pupil area of the left eye is detected as a dark part (dark pupil) by irradiation by the LED light source 103*a* or the LED light source 103*b*. As reflection of LED irradiation, a virtual image of corneal reflex of the left eye is generated, and a corneal reflection point (corneal reflection center) is detected as a bright part. That is, the position detection unit 352 detects the pupil area of the left eye from the captured image, and calculates coordinates indicating the position of the pupil center of the left eye. For example, the position detection unit 352 detects an area having predetermined brightness or less including a darkest part in a certain area including the left eye, as the pupil area, and detects an area having predetermined brightness or more including a brightest part, as the corneal reflex. Further, the position detection unit 352 detects the corneal reflex area of the left eye from the captured image, and calculates coordinates indicating the position of the corneal reflection center. Note that the position detection unit 352 calculates the coordinate value of the pupil center and the coordinate value of the corneal reflection center of the left eye, for each of the two images acquired with the right and left cameras (Step S106L).

Note that, to acquire three-dimensional world coordinates, the right and left cameras are calibrated by a stereo calibration method in advance, and conversion parameters are calculated. As the stereo calibration method, any conventional method such as a method using Tsai's camera calibration theory can be applied.

The position detection unit 352 converts the pupil center and the corneal reflection center of the left eye to three-dimensional world coordinates based on the coordinates of the right and left cameras, using the conversion parameters (Step S107L). For example, the position detection unit 352 performs the conversion into the three-dimensional world coordinates using the conversion parameters, by setting coordinates obtained from an image captured by the left camera 102*b* when the LED light source 103*a* is turned on as the coordinates of the left camera, and by setting coordinates obtained from an image captured by the right camera 102*a* when the LED light source 103*b* is turned on as the coordinates of the right camera. The world coordinate value obtained as a result of the conversion corresponds to the world coordinate value obtained from the images captured by the right and left cameras assuming that the light is radiated from the virtual light source 303. The curvature radius calculation unit 353 obtains a straight line connecting the obtained world coordinates of the corneal reflection center and the world coordinates of the center position of the virtual light source 303 (Step S108L). Next, the curvature radius calculation unit 353 calculates a straight line connecting the world coordinates of the center of the target image displayed at one point on the screen of the display unit 101 and the world coordinates of the pupil center of the left eye (Step S109L). The curvature radius calculation unit 353 obtains an intersection point of the straight line calculated in Step S108L and the straight line calculated in Step S109L, and sets the intersection point as the corneal curvature center of the left eye (Step S110L). The curvature radius calculation unit 353 calculates the distance between the pupil center and the corneal curvature center at this time and stores in the storage unit 150 (Step S111L). The distance stored is used to calculate the corneal curvature center at the time of subsequent viewpoint (visual line) detection.

The distance between the pupil center and the corneal curvature center in gazing at one point on the display unit 101 in the calibration processing is kept constant within a range for detecting a viewpoint within the display unit 101. The distance between the pupil center and the corneal curvature center may be obtained from an average of the entire values calculated during reproduction of the target image or may be obtained from an average of several values of the values calculated during the reproduction.

The curvature radius calculation unit 353 calculates the corneal curvature radius of the left eye (Step S112L). The curvature radius calculation unit 353 stores the calculated corneal curvature radius r1 of the left eye in the storage unit 150 (Step S113L).

The procedure up to the storage of the corneal curvature radius of the left eye has been described. A procedure similar to that of Steps S106L to S113L for the left eye is also performed for the right eye (Steps S106R to S113R), and the corneal curvature radius of the right eye is stored. Description of the procedure up to storage of the corneal curvature radius of the right eye is omitted.

Figure 11:
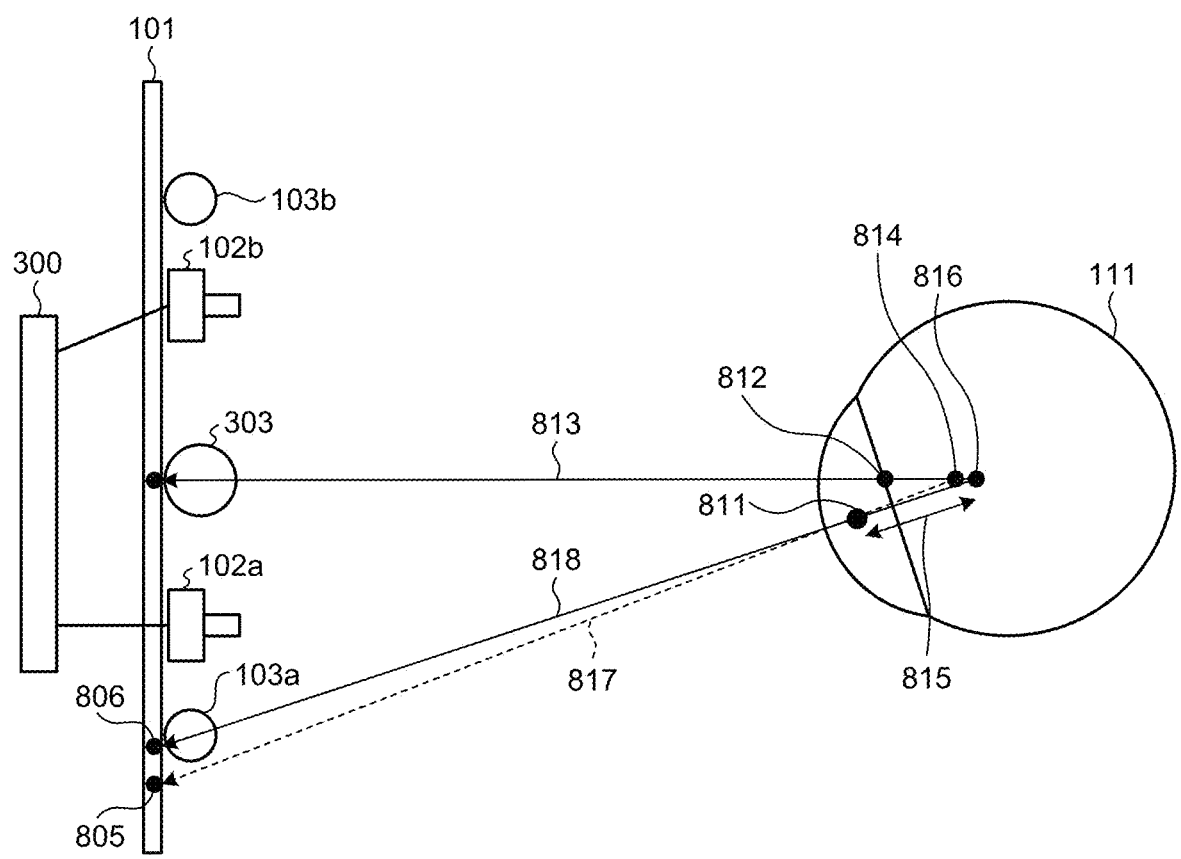
FIG. 11 is a diagram illustrating a method for calculating a position of a corneal curvature center, using the distance obtained in advance.

FIG. 11 is a diagram illustrating a method of calculating a position of a corrected corneal curvature center, using the distance between the pupil center and the corneal curvature center obtained in advance, in performing viewpoint detection. A gaze point 805 represents a gaze point obtained from the corneal curvature center calculated using a general curvature radius value. A gaze point 806 represents a gaze point obtained from the corneal curvature center calculated using a distance obtained in advance.

A pupil center 811 and a corneal reflection center 812 indicate the position of the pupil center and the position of the corneal reflection center calculated when detecting a viewpoint, respectively. A straight line 813 is a straight line connecting the virtual light source 303 and the corneal reflection center 812. A corneal curvature center 814 is the position of the corneal curvature center calculated from a general curvature radius value. A distance 815 is the distance between the pupil center and the corneal curvature center calculated by calibration processing in advance. A corneal curvature center 816 is the position of the corneal curvature center calculated using a distance obtained in advance. The corneal curvature center 816 is obtained as the corneal curvature center lies on the straight line 813 and the distance between the pupil center and the corneal curvature center is distance 815. Accordingly, a visual line 817 calculated using a general curvature radius value is corrected to a visual line 818. Further, the gaze point on the screen of the display unit 101 is corrected from the gaze point 805 to the gaze point 806.

Figure 12:
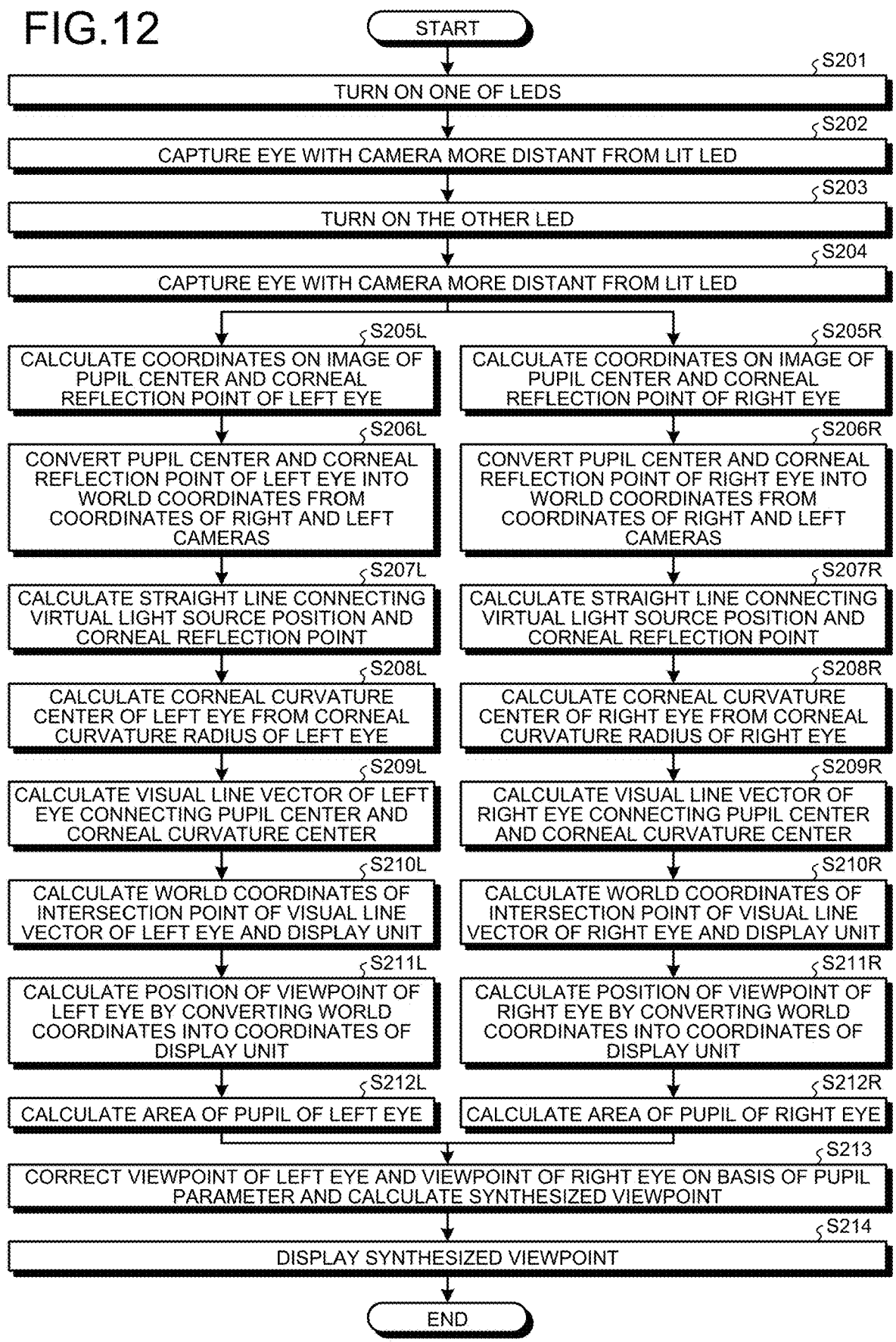
FIG. 12 is a flowchart illustrating an example of visual line detection processing of the present embodiment.

FIG. 12 is a flowchart illustrating an example of visual line detection processing of the present embodiment. First, processing from Steps S201 to S204 illustrated in FIG. 12 is executed. Steps S201 to S204 are similar to Steps S102 to S105 in FIG. 10, and thus description is omitted.

After Step S204, processing for the left eye that is the left eyeball and processing for the right eye that is the right eyeball are separately performed. First, the visual line detection processing for the left eye will be described. Note that processing from Step S205L to Step S207L illustrated in FIG. 12 is similar to the processing from Step S106L to Step S108L in FIG. 10, and thus description is omitted.

The visual line detection unit 354 calculates the world coordinate values of the pupil center and the corneal reflection center of the left eye of the subject, and calculates the corneal curvature center of the left eye of the subject on the basis of the corneal curvature radius r1 stored in the storage unit 150 in Step S113L in FIG. 10 (Step S208L). The curvature radius calculation unit 353 calculates a position, as the corneal curvature center of the left eye, existing on the straight line calculated in Step S207L and equal to the corneal curvature center of the corneal curvature radius r1 stored in the storage unit 150 in Step S113L in FIG. 10.

The visual line detection unit 354 obtains a visual line vector connecting the pupil center and the corneal curvature center of the left eye (Step S209L). This visual line vector indicates the visual line direction that the left eye of the subject views. The viewpoint detection unit 355 calculates a three-dimensional world coordinate value of an intersection point between the visual line vector of the left eye and the screen of the display unit 101 (Step S210L). This value is a coordinate value representing, by world coordinates, one point on the display unit 101, which the left eye of the subject gazes at. The viewpoint detection unit 355 converts the obtained three-dimensional world coordinate value into coordinate values (x1, y1) expressed by the two-dimensional coordinate system of the display unit 101. Accordingly, the position of the viewpoint on the display unit 101, which the left eye of the subject is gazing at, is calculated (Step S211L).

The extraction unit 357 calculates the area of the pupil of the left eye as the pupil parameter indicating the size of the pupil of the left eye, from the image of the left eye (Step S212L). The extraction unit 357 calculates the area of the pupil of the left eye of when the position of the viewpoint of the left eye is calculated. In other words, detection of the position of the viewpoint of the left eye and detection of the area of the pupil of the left eye are performed from the image obtained in the same frame.

Figure 13:
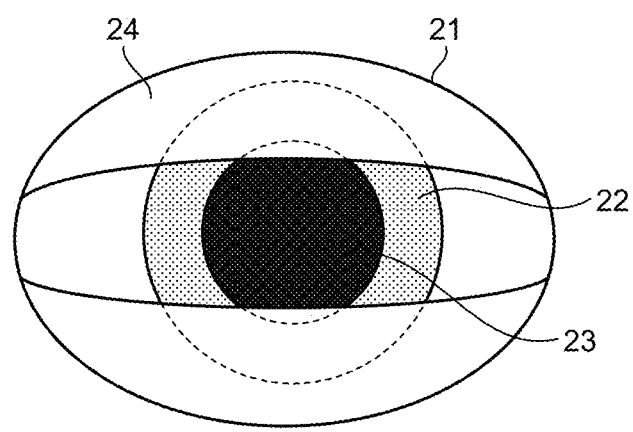
FIG. 13 is a schematic diagram illustrating an example of an eye of a subject captured with the stereo camera of the present embodiment.

The image of the left eye captured by the stereo camera is highly likely to be different depending on the timing when the capture is performed. For example, when the subject blinks or lowers his/her visual line, a part or the entirety of the pupil 23 is hidden by an eyelid 24, as illustrated in the schematic diagram in FIG. 13. In that case, the area of the pupil 23 becomes small in the image captured by the stereo camera. On the other hand, when the subject largely opens the eye, the area of the pupil 23 becomes large in the image captured by the stereo camera.

Figure 14:
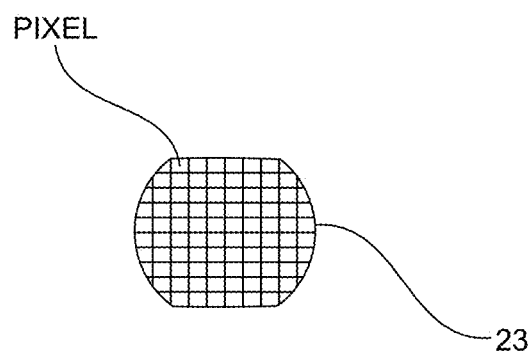
FIG. 14 is a schematic diagram illustrating a method of calculating an area of a pupil of the present embodiment.

FIG. 14 is a schematic diagram illustrating a method of obtaining the area of the pupil 23 in the captured image. The contrast of the pupil 23 and the iris 22 around or the contract of the pupil 23 and the eyelid 24 around are different. Therefore, an external form or a contour of the pupil 23 is defined in the image from the difference in contrast. By calculating the number of pixels arranged in the pupil 23 with the defined external form, the area of the pupil 23 is calculated on the basis of the area of one pixel and the number of the pixels.

The procedure up to the calculation of the coordinate values (x1, y1) of the viewpoint of the left eye (Step S211L) and the calculation of the area of the pupil of the left eye (Step S212L) has been described. A procedure similar to that of Steps S205L to S212L for the left eye is also performed for the right eye (Steps S205R to S212R). In Step S211R, coordinate values (x2, y2) of the viewpoint of the right eye are calculated, and in Step S212R, the area of the pupil of the right eye is calculated. Description of a procedure up to the calculation of the area of the pupil of the right eye is omitted.

After the position of the viewpoint of the left eye and the area of the pupil of the left eye at the viewpoint, and the position of the viewpoint of the right eye and the area of the pupil of the right eye at the viewpoint are calculated, the correction unit 358 corrects the viewpoint of the left eye and the viewpoint of the right eye on the basis of the pupil parameters so as to calculate the synthesized viewpoint (Step S213).

The correction unit 358 corrects the position of the viewpoint of the left eye and the position of the viewpoint of the right eye on the basis of the area of the pupil of the left eye and the area of the pupil of the right eye calculated in Steps S212L and S212R. In the case where the coordinate values of the position of the viewpoint of the left eye is (x1, y1), the coordinate value of the position of the viewpoint of the right eye is (x2, y2), the area of the pupil of the left eye is SL, and the area of the pupil of the right eye is SR, the correction unit 358 calculates the position of the synthesized viewpoint (xa, ya) by performing arithmetic processing of the following expression (1).

$$(xa, ya) = (x1, y1) \times SL/(SR+SL) + (x2, x2) \times SR/(SR+SL) \quad (1)$$

As illustrated in the expression (1), the correction by the correction unit 358 includes giving weights to the position of the viewpoint of the left eye and the position of the viewpoint of the right eye using the areas SL and SR of the right and left pupils. The correction unit 358 makes a weight to be given to the position of the viewpoint of the eyeball having a larger pupil parameter (a larger area of the pupil) between the pupils of the right and left eyeballs larger than a weight to be given to the position of the viewpoint of the eyeball having a smaller pupil parameter (a smaller area of the pupil), on the basis of the extracted pupil parameters. For example, in the case where the area SL of the pupil of the left eye is larger than the area SR of the pupil of the right eye, the weight to be given to the viewpoint of the left eye is larger than the weight to be given to the viewpoint of the right eye.

The pupil center is calculated as a center of a circle that passes through a plurality of points that is selected from points on a contour of a pupil area appearing in the image. Typically, the ratio of the pupil hidden by the eyelid becomes smaller as the area of the pupil is larger, and the pupil center can be accurately obtained. Therefore, in the case of calculating the synthesized viewpoint of the left eye and the right eye, the weight to be given to the viewpoint of the eyeball with the larger pupil area is made larger than the weight to be given to the viewpoint of the eyeball with the smaller pupil area, whereby the position (xa, ya) of the synthesized viewpoint can be calculated with high precision.

The output control unit 356 displays the synthesized viewpoint having the calculated coordinate values (xa, ya) on the display unit 101 (Step S214).

Figure 15:
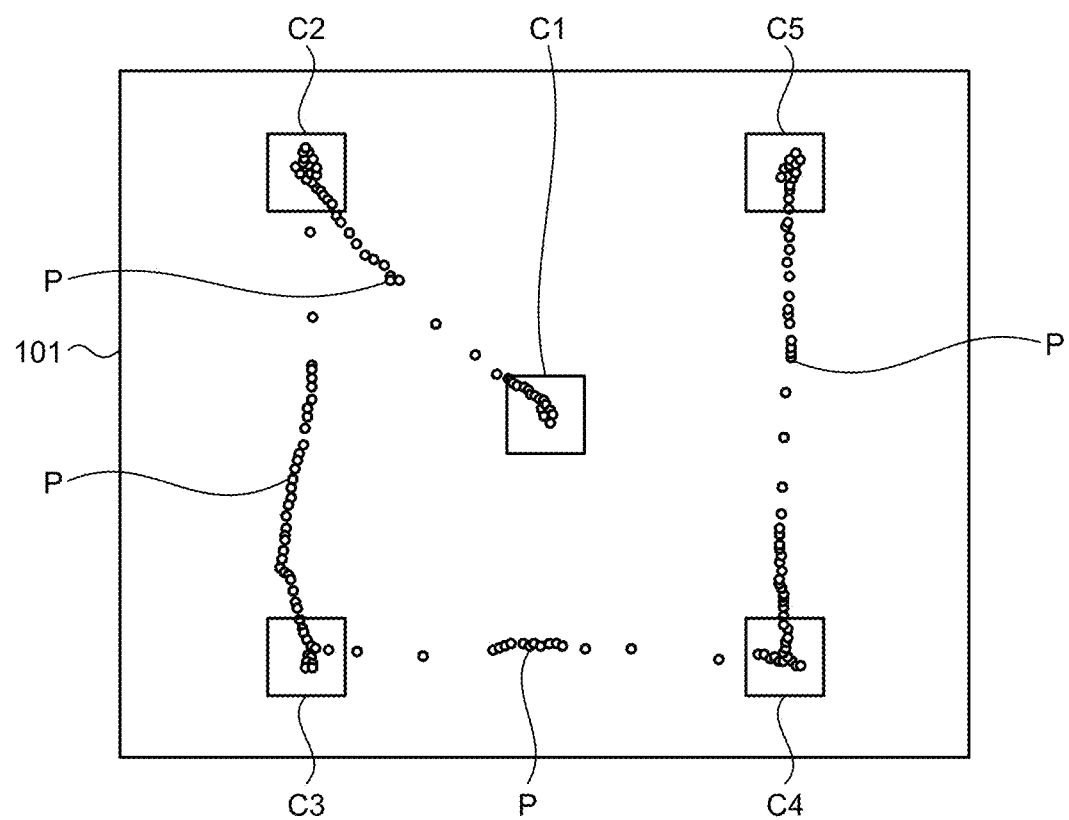
FIG. 15 is a diagram illustrating a display example of the display unit of the present embodiment.

FIG. 15 is a diagram illustrating an example of viewpoints displayed on the display unit 101 by the output control unit 356 in Step S214. As illustrated in FIG. 15, index images C1, C2, C3, C4, and C5 are displayed on the display unit 101. To evaluate how the eyeballs of the subject move, the subject is instructed to move the viewpoints of both the right and left eyeballs in order of the index images C1, C2, C3, C4, and C5.

A plot point P indicating a synthesized viewpoint obtained by synthesizing viewpoints of both the right and left eyeballs is displayed on the display unit 101. After the detection and synthesis of the viewpoints are performed, an operation input unit provided in the diagnosis support apparatus 100 is operated by an operator or the subject, and the plot point P is displayed on the display unit 101 by the operation. Detection of the viewpoints is performed at a cycle (for example, every 50 [msec]) of frame synchronization signals output from the right and left cameras. Therefore, a larger interval between the plot points P indicates faster movement of the viewpoints.

As described above, according to the present embodiment, the pupil parameters indicating the sizes of the pupils of the right and left respective eyeballs are extracted, and the position of the viewpoint of the left eyeball and the position of the viewpoint of the right eyeball are corrected on the basis of the pupil parameters and the synthesized viewpoint is calculated. Therefore, the position of the synthesized viewpoint can be calculated with high precision.

Further, typically, the ratio of the pupil hidden by the eyelid becomes smaller as the area of the pupil is larger, and the pupil center can be accurately obtained. Therefore, by adopting the area of the pupil as the pupil parameter, the position of the synthesized viewpoint can be calculated with high precision.

Further, the weight to be given to the position of the viewpoint of the eyeball having a larger area of the pupil between the right and left eyeballs is made larger, whereby the position of the synthesized viewpoint can be calculated with high precision.

Further, when the synthesized viewpoint calculated with high precision is displayed on the display unit 101, the operator or the subject can accurately grasp the movement of the viewpoint by viewing the display unit 101.

Note that the pupil parameter is not necessarily the area of the pupil acquired in the image. The pupil parameter may be the external form of the pupil acquired in the image, the length of a circular arc portion of the contour of the pupil, or an aspect ratio of the pupil in the image. The long circular arc portion of the contour of the pupil means that the eyelid of the subject is open, and the short circular arc portion of the contour of the pupil means that the eyelid of the subject is close. Further, approximation of a horizontal dimension and a vertical dimension of the pupil means that the eyelid of the subject is open, and the horizontal dimension of the pupil being larger than the vertical dimension of the pupil means that the eyelid of the subject is close.

(Modification)

The calibration processing of calculating the distance between the pupil center position and the corneal curvature center position is not limited to the method described with reference to FIGS. 9 and 10. Hereinafter, another example of the calculation processing will be described with reference to FIGS. 16 and 17.

Figure 16:
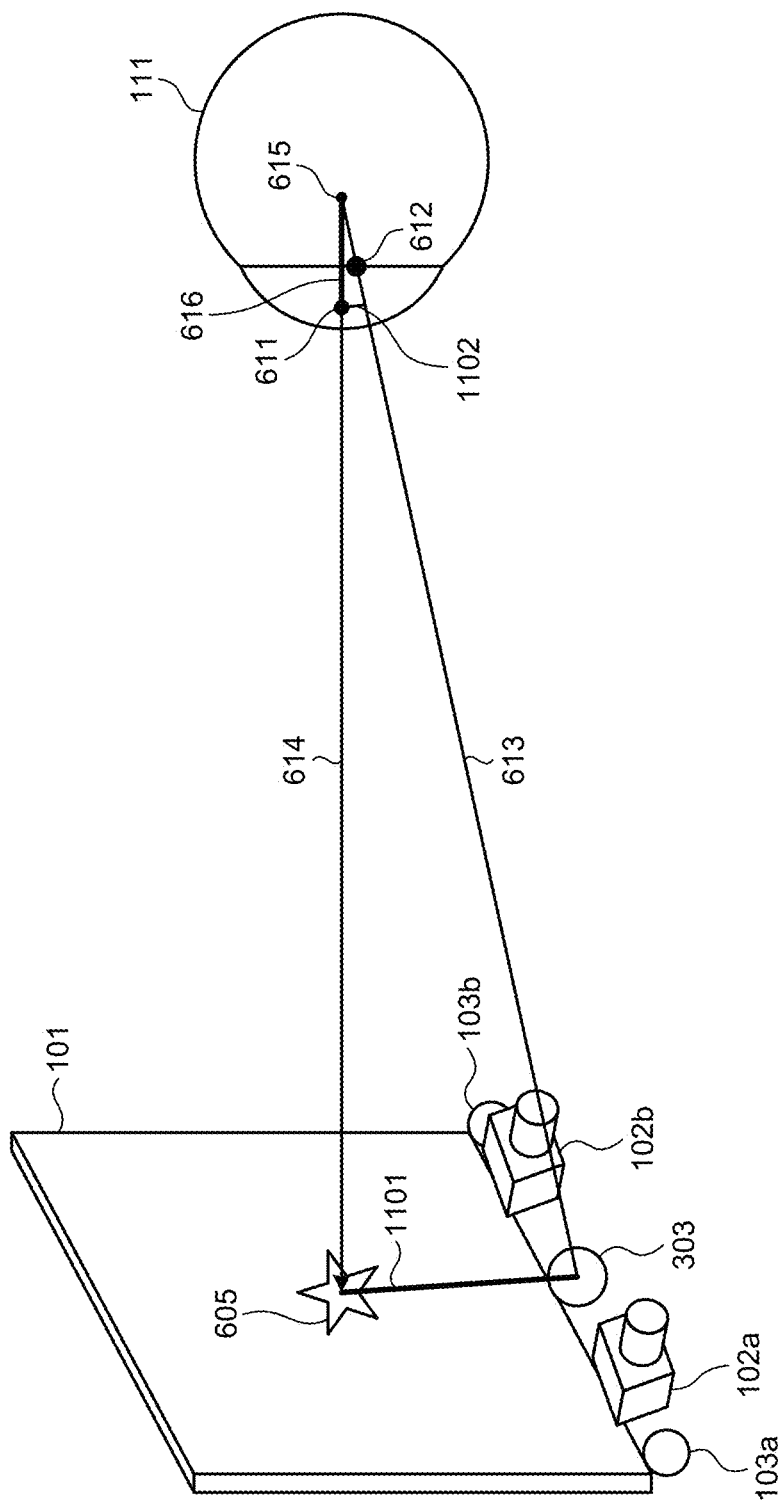
FIG. 16 is a diagram for describing calculation processing of a modification.

FIG. 16 is a diagram for describing calculation processing of the present modification. The same reference numerals are given to elements that have been described in FIGS. 3 to 6, and 9, and description of the elements is omitted.

A line segment 1101 is a line segment (first line segment) connecting a target position 605 and a virtual light source position. A line segment 1102 is a line segment (second line segment) that is parallel to the line segment 1101 and connects a pupil center 611 and a straight line 613. In the present modification, a distance 616 between the pupil center 611 and a corneal curvature center 615 is calculated using the line segment 1101 and the line segment 1102, and stored as described below.

Figure 17:
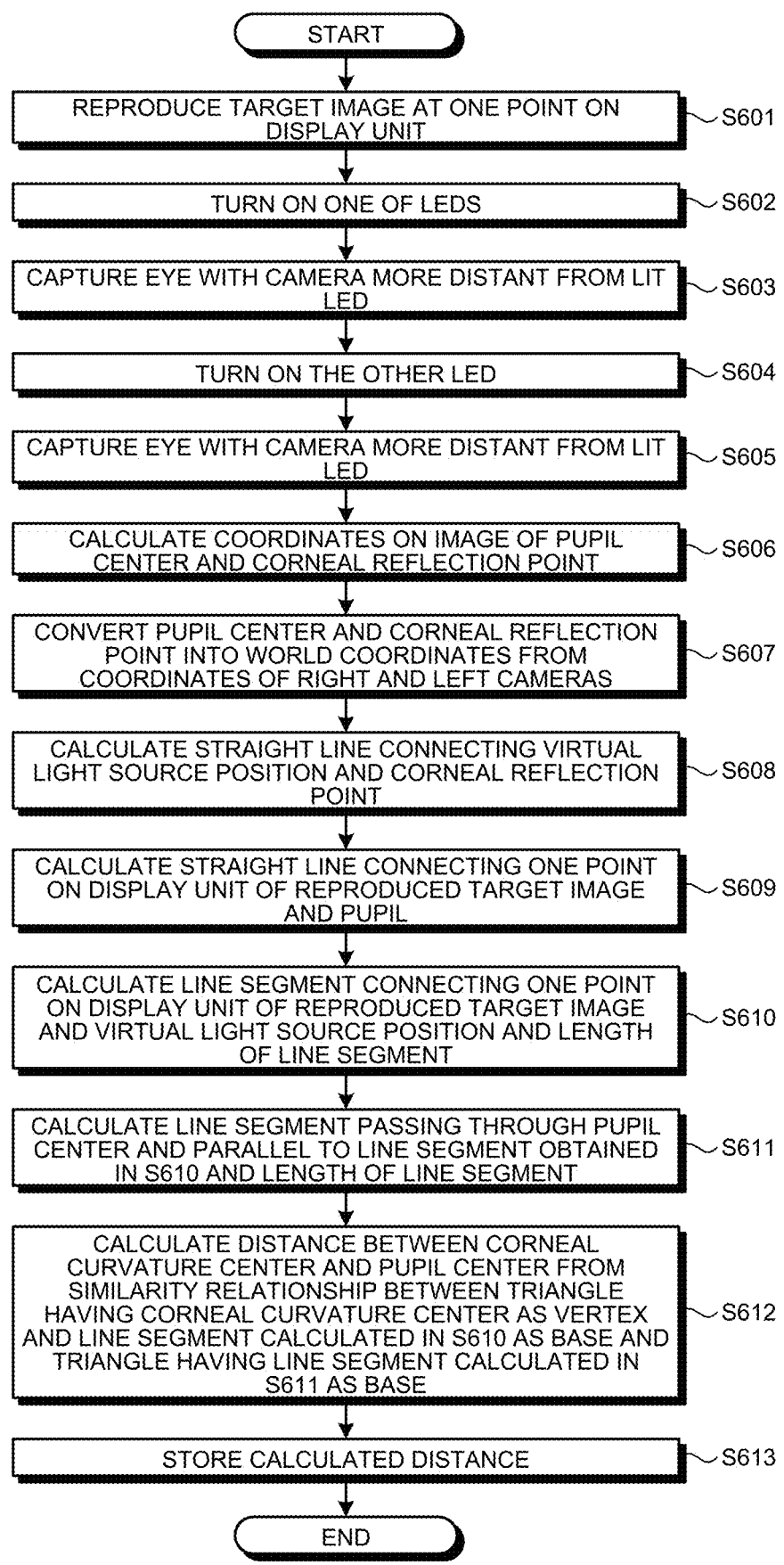
FIG. 17 is a flowchart illustrating an example of the calculation processing of the modification.

FIG. 17 is a flowchart illustrating an example of calculation processing of the present modification. Note that FIG. 17 illustrates processing for one of right and left eyeballs.

Steps S601 to S609 are similar to Steps S101 to S109L in FIG. 10, and thus description is omitted.

A curvature radius calculation unit 353 calculates a line segment (a line segment 1101 in FIG. 16) connecting a center of a target image displayed at one point on a screen of a display unit 101 and the virtual light source position, and calculates a length (L1101) of the calculated line segment (Step S610).

The curvature radius calculation unit 353 calculates a line segment (a line segment 1102 in FIG. 16) passing through the pupil center 611 and parallel to the line segment calculated in Step S610, and calculates a length (L1102) of the calculated line segment (Step S611).

The curvature radius calculation unit 353 calculates the distance 616 between the pupil center 611 and the corneal curvature center 615 on the basis of the fact that a triangle having the corneal curvature center 615 as a vertex and having the line segment calculated in Step S610 as a base, and a triangle having the corneal curvature center 615 as a vertex and having the line segment calculated in Step S611 as a base are in a similarity relationship (Step S612). For example, the curvature radius calculation unit 353 calculates the distance 616 such that a ratio of the length of the line segment 1102 to the length of the line segment 1101 and a ratio of the distance 616 to the distance between the target position 605 and the corneal curvature center 615 become equal.

The distance 616 can be calculated by the following expression (2). Note that L614 is a distance from the target position 605 to the pupil center 611.

$$\text{The distance } 616 = (L614 \times L1102)/(L1101 - L1102) \qquad (2)$$

The curvature radius calculation unit 353 stores the calculated distance 616 in the storage unit 150 or the like (Step S613). The stored distance is used to calculate the corneal curvature center at the time of subsequent viewpoint (visual line) detection.

The visual line detection apparatus and the visual line detection method according to the present disclosure exhibit an effect to accurately calculate a pupil center and accurately detect a viewpoint of a subject.

REFERENCE SIGNS LIST

11 EYE
12 IRIS
13 PUPIL
21 EYE
22 IRIS
23 PUPIL
24 EYELID
100 DIAGNOSIS SUPPORT APPARATUS
101 DISPLAY UNIT
102a RIGHT CAMERA
102b LEFT CAMERA

103a LED LIGHT SOURCE
103b LED LIGHT SOURCE
111 EYEBALL
112 PUPIL
113 CORNEAL REFLEX
150 STORAGE UNIT
201 DISPLAY SCREEN
203 LED LIGHT SOURCE
205 SPEAKER
300 CONTROL UNIT
303 VIRTUAL LIGHT SOURCE
313 DRIVE/IF UNIT
314 CAMERA IF
315 CAMERA IF
316 LED DRIVE CONTROL UNIT
322 SPEAKER DRIVE UNIT
351 LIGHTING CONTROL UNIT
352 POSITION DETECTION UNIT
353 CURVATURE RADIUS CALCULATION UNIT
354 VISUAL LINE DETECTION UNIT
355 VIEWPOINT DETECTION UNIT
356 OUTPUT CONTROL UNIT
357 EXTRACTION UNIT
358 CORRECTION UNIT
407 PUPIL CENTER
408 CORNEAL REFLECTION CENTER
409 CORNEAL CURVATURE RADIUS
505 CORNEAL CURVATURE CENTER
509 CORNEAL CURVATURE RADIUS
523 STRAIGHT LINE
605 TARGET POSITION
609 CORNEAL CURVATURE RADIUS
611 PUPIL CENTER
612 CORNEAL REFLECTION CENTER
613 STRAIGHT LINE
614 STRAIGHT LINE
615 CORNEAL CURVATURE CENTER
616 DISTANCE
621 CORNEAL REFLECTION POINT
622 CORNEAL REFLECTION POINT
624 CORNEAL REFLECTION POINT
805 GAZE POINT
806 GAZE POINT
811 PUPIL CENTER
812 CORNEAL REFLECTION CENTER
813 STRAIGHT LINE
814 CORNEAL CURVATURE CENTER
815 DISTANCE
816 CORNEAL CURVATURE CENTER
817 VISUAL LINE
818 VISUAL LINE

What is claimed is:

1. A visual line detection apparatus comprising:
a light source configured to irradiate an eyeball of a subject with detection light;
an imaging unit configured to image the eyeballs irradiated with the detection light;
a position detection unit configured to detect positions of pupil centers indicating centers of pupils of right and left respective eyeballs and positions of corneal reflection centers indicating centers of corneal reflexes from an image of the eyeballs imaged by the imaging unit;
a curvature radius calculation unit configured to calculate corneal curvature radii of the right and left respective eyeballs from a position of the light source and the positions of the corneal reflection centers;
a viewpoint detection unit configured to detect viewpoints of the right and left respective eyeballs from the positions of the pupil centers and the corneal curvature radii;
an extraction unit configured to extract, as pupil parameters, size of areas of the pupils of the right and left respective eyeballs acquired in the image of the eyeballs based on the same image as the image used for detecting viewpoints of the right and left respective eyeballs by the viewpoint detection unit, every time the viewpoint detection unit detects viewpoints of the right and left respective eyeballs; and
a calculation unit configured to calculate synthesized viewpoint by adding weights based on the pupil parameters to the viewpoints of the right and left respective eyeballs detected by the viewpoint detection unit.

2. The visual line detection apparatus according to claim 1, wherein
the calculation unit makes a weight to be given to the viewpoint of the eyeball having a larger pupil parameter between the pupils of the right and left eyeballs larger than a weight to be given to the viewpoint of the eyeball having a smaller pupil parameter on the basis of the extracted pupil parameters.

3. The visual line detection apparatus according to claim 1, further comprising:
an output control unit configured to display the calculated synthesized viewpoint on a display unit.

4. A visual line detection method comprising steps of:
irradiating an eyeball of a subject with detection light emitted from a light source;
imaging the eyeballs irradiated with the detection light;
detecting positions of pupil centers indicating centers of pupils of right and left respective eyeballs and positions of corneal reflection centers indicating centers of corneal reflexes from an image of the eyeballs which are imaged;
calculating corneal curvature radii of the right and left respective eyeballs from a position of the light source and the positions of the corneal reflection centers;
detecting viewpoints of the right and left respective eyeballs from the positions of the pupil centers and the corneal curvature radii;
extracting, as pupil parameters, size of areas of the pupils of the right and left respective eyeballs acquired in the image of the eyeballs based on the same image as the image used for detecting viewpoints of the right and left respective eyeballs, every time viewpoints of the right and left respective eyeballs are detected; and
calculating synthesized viewpoint by adding weights based on the pupil parameters to the detected viewpoints of the right and left respective eyeballs.

5. The visual line detection apparatus according to claim 2, wherein
the calculation unit calculates a position of the synthesized viewpoint such that a distance from the position of the synthesized viewpoint to a first position is shorter than a distance from the position of the synthesized viewpoint to a second position, the first position is a position of a viewpoint of an eyeball of which area of the pupil is larger than an area of the pupil of an other eyeball in the right and left eyeballs, and the second position is a position of a viewpoint of an eyeball of which the pupil parameter is smaller than the pupil parameter of the other eyeball in the right and left eyeballs.

6. The visual line detection apparatus according to claim 1, wherein
the pupil parameter is area of pupil, external form of pupil, length of a circular arc position of contour of pupil, or aspect ratio of pupil which are acquired by the image of the eyeballs, wherein,
the calculation unit calculates the synthesized viewpoint based on ratio of values of the pupil parameters between the right and left eyeballs.

* * * * *